(12) United States Patent
Lutz et al.

(10) Patent No.: US 7,010,991 B2
(45) Date of Patent: Mar. 14, 2006

(54) SURFACE PARTICLE DETECTOR (75) Inventors: Donald G. Lutz, San Ramon, CA (US);
Daniel Duggan, Danville, CA (US)

(73) Assignee: Pentagon Technologies Group, Inc., Fremont, CA (US)

( * ) Notice: Subject to any disclaimer, the term of this patent is extended or adjusted under 35 U.S.C. 154(b) by 183 days.

(21) Appl. No.: 09/952,900

(22) Filed: Sep. 11, 2001

(65) Prior Publication Data

US 2002/0083780 A1 Jul. 4, 2002

Related U.S. Application Data (60) Provisional application No. 60/232,267, filed on Sep. 13, 2000.

(51) Int. Cl.
*G01N 1/00* (2006.01)

(52) U.S. Cl. .................................. 73/864.33; 73/864.71
(58) Field of Classification Search .............. 73/864.71, 73/864.33, 864.34, 864.81, 863.23, 863.25, 73/863.01, 863.02, 863.03, 865.5; 356/440, 356/437

See application file for complete search history.

(56) References Cited

U.S. PATENT DOCUMENTS

| | | | |
|---|---|---|---|
| 3,653,253 A | | 4/1972 | Olin |
| 4,298,860 A | | 11/1981 | Norberg et al. |
| 4,527,953 A | * | 7/1985 | Baker et al. ............. 73/863.23 |
| 4,569,235 A | * | 2/1986 | Conkle et al. ........... 73/863.23 |
| 4,682,993 A | | 7/1987 | Todd et al. |
| 4,909,090 A | * | 3/1990 | McGown et al. ......... 73/864.33 |
| 4,941,105 A | | 7/1990 | Marangoni |
| 4,962,368 A | | 10/1990 | Dobrzanski et al. |
| 5,125,480 A | | 6/1992 | Gregory et al. |
| 5,248,933 A | | 9/1993 | Venditti |
| 5,253,538 A | | 10/1993 | Swick et al. |
| 5,404,762 A | * | 4/1995 | Rodgers et al. .......... 73/863.25 |

(Continued)

FOREIGN PATENT DOCUMENTS

| | | |
|---|---|---|
| EP | 0 388 993 A1 | 9/1990 |
| JP | 1-245131 | 9/1989 |
| JP | 11-226017 | 8/1999 |

*Primary Examiner*—Robert Raevis
(74) *Attorney, Agent, or Firm*—DLA Piper Rudnick Gray Cary US LLP (57) ABSTRACT

A surface particle detector that includes a scanner slidable over a surface, a particle counter for counting particles passed therethrough, and a conduit connected between the scanner and the particle counter. The particle counter includes a pump for creating an airstream for drawing particles from the surface, through the scanner and conduit, to the particle counter, and back to the scanner. A sensor measures the airstream flow rate, and a controller controls the pump speed based upon the sensed airstream flow rate. The conduit attaches to the particle counter via a first connector, which contains electronic indicia identifying the type of scanner attached to the other end of the conduit. The controller controls the particle counter in response to the detected electronic indicia. The particle counter also includes a removable filter cartridge with a filter element that captures the counted particles for laboratory analysis.

18 Claims, 10 Drawing Sheets

U.S. PATENT DOCUMENTS

| | | |
|---|---|---|
| 5,440,301 A | 8/1995 | Evans |
| 5,501,113 A | 3/1996 | Harrison et al. |
| 5,526,576 A | 6/1996 | Fuchs et al. |
| 5,591,974 A | 1/1997 | Troyer et al. |
| 5,642,284 A | 6/1997 | Parupalli et al. |
| 5,872,512 A | 2/1999 | Kackman et al. |
| 5,878,377 A | 3/1999 | Hamilton, II et al. |
| 5,892,690 A | 4/1999 | Boatman et al. |
| 5,920,392 A | 7/1999 | Tsai et al. |
| 5,925,825 A | 7/1999 | Cochimin |
| 5,930,744 A | 7/1999 | Koch et al. |
| 5,939,647 A | 8/1999 | Chinn et al. |
| 5,940,784 A | 8/1999 | El-Husayni |
| 5,949,001 A | 9/1999 | Willeke |
| 5,974,868 A * | 11/1999 | Decain et al. .............. 73/61.72 |
| 6,055,480 A | 4/2000 | Nevo et al. |
| 6,073,036 A | 6/2000 | Heikkinen et al. |
| 6,076,392 A | 6/2000 | Drzewiecki |
| 6,103,534 A | 8/2000 | Stenger et al. |
| 6,167,107 A | 12/2000 | Bates |
| 6,405,135 B1 | 6/2002 | Adriany et al. |
| 6,460,005 B1 | 10/2002 | Chang |
| 6,473,660 B1 | 10/2002 | Thibault |
| 6,525,658 B1 | 2/2003 | Streetman et al. |
| 6,529,591 B1 | 3/2003 | Dosani et al. |
| 6,583,720 B1 | 6/2003 | Quigley |
| 6,661,345 B1 | 12/2003 | Bevan et al. |

* cited by examiner

SURFACE PARTICLE DETECTOR

This application claims the benefit of U.S. Provisional Application No. 60/232,267, filed Sep. 13, 2000, and entitled Improved Surface Particle Detector.

FIELD OF THE INVENTION

This invention relates generally to particle counting for clean room applications, and relates more particularly to an improved device for moving particles off of a surface and into a particle counter and a filter for the purpose of ascertaining contamination levels.

BACKGROUND OF THE INVENTION

Contamination detection and quantification requirements have become increasingly important, particularly with the rapid evolution of high-tech industries. For example, the semiconductor industry has developed technology for precisely producing microelectronic devices. In order to reliably produce such products, highly stringent contamination standards must be maintained in the production facilities.

In an effort to control and minimize contamination in crucial stages of a production process, "cleanrooms" are frequently used. A cleanroom is a room in which the air filtration, air distribution, utilities, materials of construction, equipment, and operating procedures are specified and regulated to control airborne particle concentrations to meet appropriate airborne particulate cleanliness classifications.

It is important to monitor the cleanliness/contamination levels in a cleanroom, especially for detecting particles on a cleanroom surface. Visual inspection techniques have been used with ultraviolet or oblique white light. Ultraviolet light is employed to take advantage of the fact that certain organic particles fluoresce. Alternatively, white light is shined towards the test surface at an angle so as to produce reflections that can be visualized. While the white light technique is slightly more sensitive than the ultraviolet technique, they both suffer from the same limitations. These visual inspection techniques only allow a cursory inspection of the surface conditions. They do not provide quantitative data. Also, the visual inspection techniques, at best, only detect particles that are larger than twenty microns. It is often desirable to detect particles that are less than one micron.

Another inspection technique involves removing particles from a test surface, by for example, applying a piece of adhesive tape to the test surface. The particles on the tape are then manually quantified by putting the tape under a microscope and visually counting the particles. This technique allows the detection of particles of approximately five microns or larger. The primary disadvantage of this technique is that it is very time consuming, and that it is highly sensitive to variability between operators.

A third inspection technique is disclosed in U.S. Pat. No. 5,253,538, which is expressly incorporated herein by reference. The '538 patent discloses a device that includes a scanner having at least one opening for receiving particles from the sample surface. The scanner is connected to a tube having first and second ends. The first end of the tube is connected to the scanner and the second end of the tube is connected to a particle counter that employs optical laser technology. The particle counter includes a vacuum generator that causes air to flow from the sample surface through the scanner, through the tube and into the particle counter, where particles contained in the air stream are counted. The '538 patent discloses an inspection method that involves the use of the particle counting device. A background particle level of zero is first established by holding the scanner near the cleanroom supply air and taking repeated readings, or by installing an optional zero-count filter in the particle counter. Next, the hand-held scanner is passed over the sample surface at a constant rate for a predetermined test period. The test cycle is started by pushing the run switch, which is located on the scanner. The particle counter counts and reads out a number corresponding to the average number of particles per unit area. The process is usually repeated several times along adjacent surface areas, each time yielding a "test reading".

SUMMARY OF THE INVENTION

The present invention is a device for counting particles on a sample surface. The device includes a scanner having at least one opening for receiving particles from a sample surface, a particle counter for counting particles passed therethrough, a conduit having a first end connected to the scanner and a second end connected to the particle counter, wherein the conduit includes first and second tubes, a sensor and a controller. The particle counter includes a pump for producing an airstream flowing from the scanner opening, through the first tube, through the particle counter, and back to the scanner via the second tube, for carrying the particles to the particle counter for quantitation. The sensor measures a rate of flow of the airstream. The controller controls a speed of the pump in response to the measured rate of flow of the airstream to maintain the airstream at a constant flow rate while the particle counter quantitates the particles in the airstream.

In another aspect of the present invention, the device includes a scanner having at least one opening for receiving particles from a sample surface, a conduit having a first end connected to the scanner and a second end terminating in a first connector, wherein the conduit includes first and second tubes; a particle counter, electronic indicia, and a controller. The particle counter counts particles passed therethrough, and includes a port for receiving the first connector and a pump for producing an airstream flowing from the scanner opening, through the first tube, through the particle counter, and back to the scanner via the second tube, for carrying the particles to the particle counter for quantitation. The electronic indicia is disposed in at least one of the first connector, the conduit and the scanner for identifying at least one characteristic of the scanner. The controller detects the electronic indicia via the port and first connector, and controls the particle counter in response to the detected electronic indicia.

In yet one more aspect of the present invention, the device includes a scanner having at least one opening for receiving particles from a sample surface, a particle counter for analyzing particles passed therethrough, and a conduit having a first end connected to the scanner and a second end connected to the particle counter. The conduit includes first and second tubes. The particle counter includes a pump for producing an airstream flowing from the scanner opening, through the first tube, through the particle counter, and back to the scanner via the second tube, for carrying the particles to the particle counter. The particle counter also includes a particle detector for counting the particles in the airstream coming from the scanner, a filter cartridge port through which the airstream flows after passing through the particle detector, and a filter cartridge removably connected to the filter cartridge port for capturing the particles in the airstream after being counted by the particle detector.

Other objects and features of the present invention will become apparent by a review of the specification, claims and appended figures.

DETAILED DESCRIPTION OF THE PREFERRED EMBODIMENTS

The present invention is an improved surface particle detector, relative to the particle detector disclosed in U.S. Pat. No. 5,253,538, which is expressly incorporated herein by reference. The present invention advantageously employs in operable combination three primary elements to provide the flexibility of conveniently sampling particles on a wide variety of surfaces, while also providing relative quantitative data with a high degree of precision and repeatability. In broad terms, the invention involves the combination of a state-of-the-art particle counter connected to one of a plurality of specially designed and sized sampling scanners via a flexible conduit. In a preferred embodiment the conduit has two air tubes and electrical wires for supplying and returning air to and from the sample surface and for powering the scanner. The light weight moveable scanner and flexible tube design allow particle sampling on many different types of accessible surfaces. The sample surface may or may not be substantially flat, and may or may not be smooth.

Figure 1A:
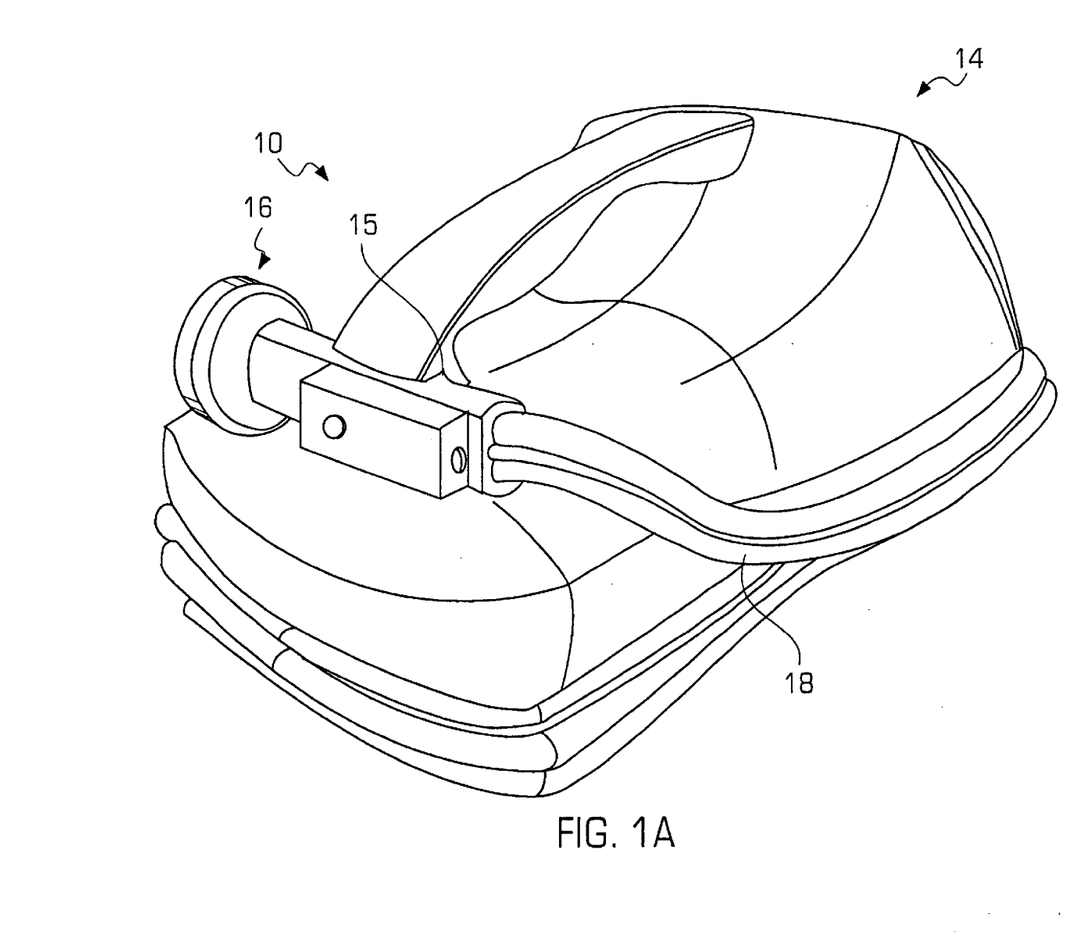
FIG. 1A is a perspective view of the particle detector of the present invention.
Figure 1B:
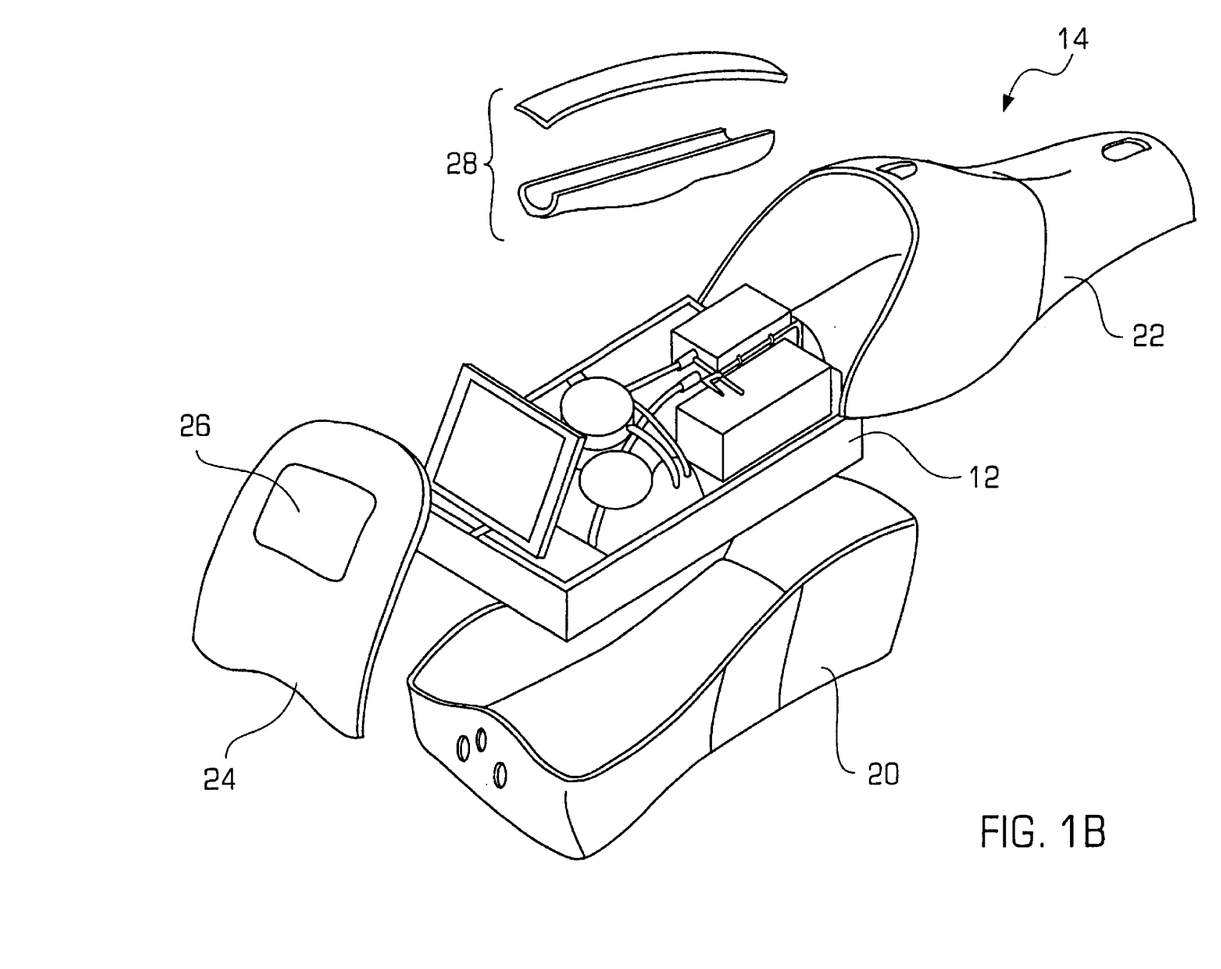
FIG. 1B is a partially broken away view of the particle detector of the present invention.

FIGS. 1A and 1B show the primary components of the particle detector 10 for analyzing particles on a sample surface. The main detector components include a particle counter assembly 12, a housing 14 surrounding the particle counter assembly 12, a scanner probe 16, and conduit 18 connected between the particle counter assembly 12 and probe 16.

Housing 14 includes a base 20, a shaped top cover 22, a front plate 24 with an aperture 26 for viewing a display, and a handle 28. These housing components are shaped to enclose particle counter assembly 12 in a small, lightweight, portable package. The housing can include a heatsink 27 for dissipating heat generated inside the unit. Preferably, housing 14 includes a small circulating fan 29 to normalize air temperature inside the unit so that the unit does not overheat.

Figures 2A, 2B:
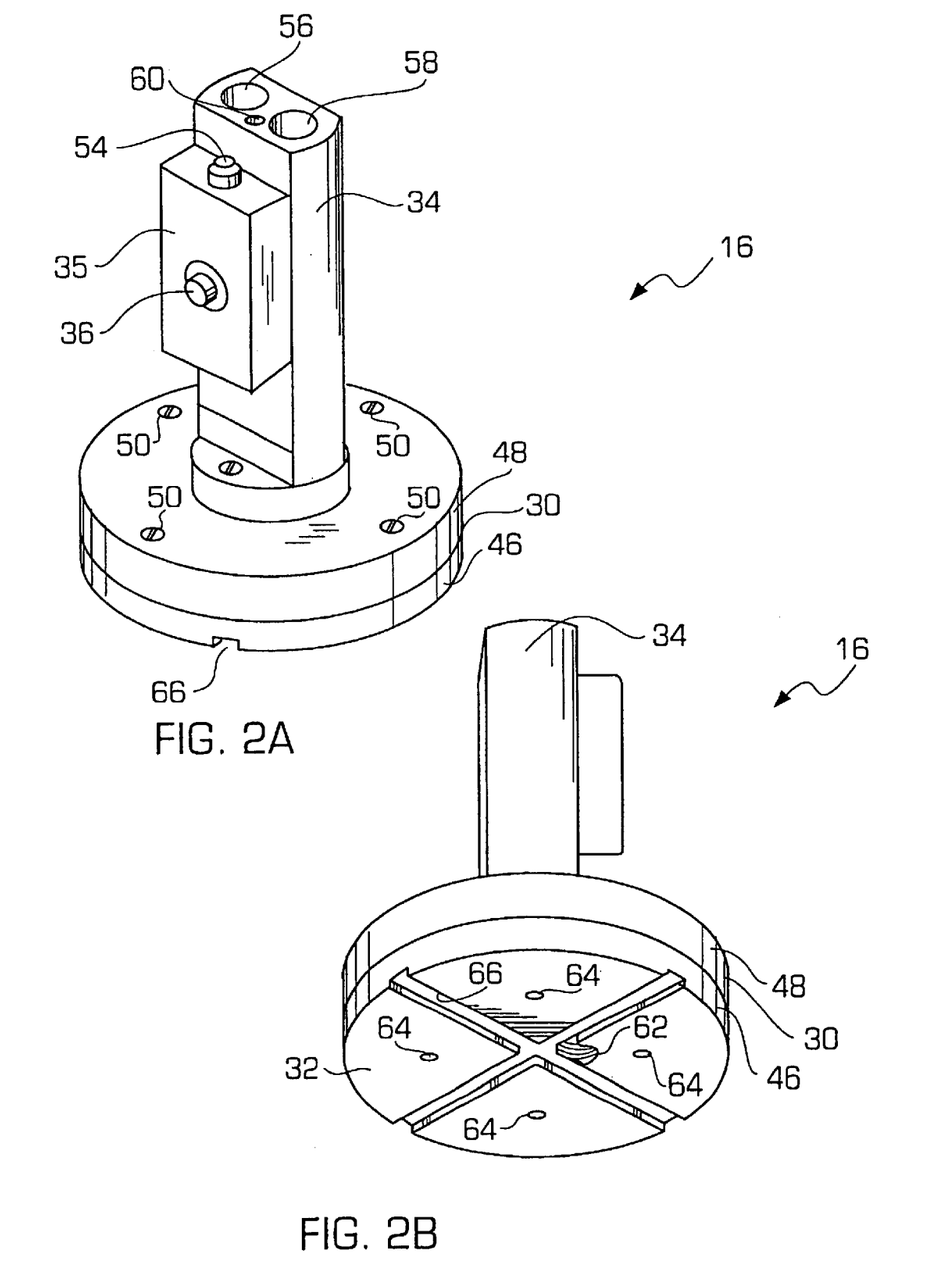
FIGS. 2A and 2B are top and bottom perspective views of the scanner of the present invention.

FIGS. 2A and 2B illustrate the scanner probe 16, which includes a substantially planar base 30. The scanner base 30 has a bottom side 32 for interfacing with the sample surface. The scanner base 30 is perpendicularly connected to a scanner handle 34 which includes a control section 35 having run switch 36 for activating the particle detector and an LED light indicating that particle counting is in progress. The conduit 18 includes a pair of tubes 38 and 40 (supply and return hoses) each having a first and a second end. The first ends of the tubes 38/40 are connected to the scanner handle 34, and the second ends are connected to a port 92 in the particle counter assembly 12. The conduit 18 also includes electrical wiring 44 which electrically connects the scanner probe 16 to the particle counter 12. The scanner probe 16 fits into a receptacle 15 in the housing 16 for easy storage.

The base portion 30 of the scanner probe 16 has two coin-shaped portions 46 and 48 which are fastened together by screws 50. The scanner embodiment shown in FIGS. 2A and 2B is designed primarily for picking up particles off of a substantially flat surface. However, scanners of other shapes which are specifically designed to conform to non-flat sample surfaces could also be used. Coin-shaped portion 46 of the scanner base 30 is also referred to as a face plate, and is preferably made of a material which is impregnated with a friction limiting non-particulating substance, for example, hard black anodized aluminum with Teflon impregnation, type 3, class 2, mil spec A8625D. The scanner handle 34 has two bores 56 and 58 for receiving the supply and return tubes 38/40. Another hole 60 is provided in the handle 34 for receiving the electrical wiring 44 from the conduit 18.

The scanner base bottom side 32 is designed to interface with the sample surface. In this embodiment, the bottom side 32 has a hole 62 which is located approximately in the center of the base plate bottom side 32. The hole 62 is connected to the bore 56 in the scanner handle 34 which is connected to the return tube 40 of conduit 18. Particles from the sample surface are sucked through the face plate hole 62 for the purpose of counting the particles in the particle counter assembly 12. The base plate bottom side 32 also has a plurality of smaller holes 64 which converge into the scanner handle bore 58, which is connected to the air supply tube 38 of conduit 18. Air is supplied from the particle counter assembly 12 and delivered through the face plate holes 64 onto the sample surface for dislodging and fluidizing particles so that they may be sucked through face plate hole 62 for counting. Face plate bottom side 32 also has intersecting grooves 66 for channeling dislodged particles into face plate hole 62.

Figure 3:
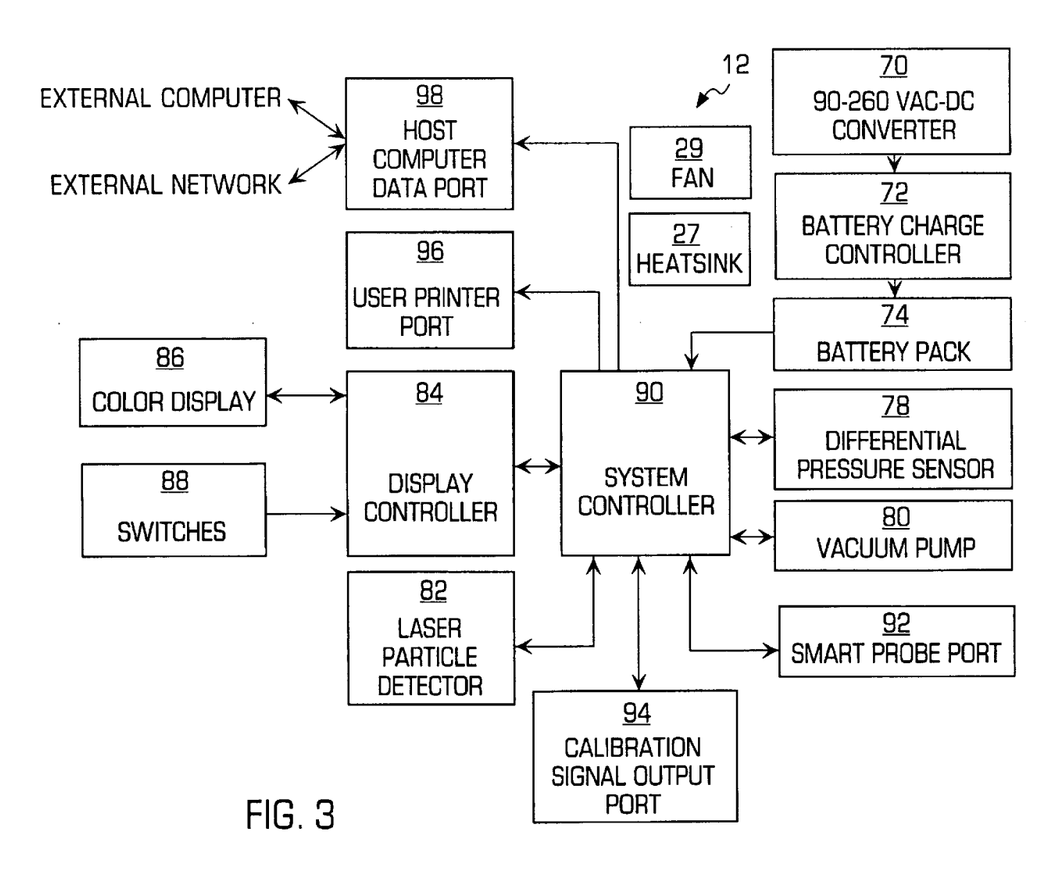
FIG. 3 is a block schematic diagram of the particle counter assembly of the present invention.

FIG. 3 schematically shows the particle counter assembly 12, which includes a 90–260 VAC-DC converter 70, a battery charge controller 72, a batter pack 74, a differential pressure sensor 78, a vacuum pump 80, a laser particle detector 82, a display controller 84 for controlling a color display 86 and receiving input from switches 88 located on a control panel, all controlled by a system controller 90. A series of ports are also connected to the controller 90, including a smart probe port 92, a calibration signal output port 94, a user printer port 96, and a host computer data port 98. In a preferred embodiment, the controller 90 also includes software for converting numbers of detected particles to numbers of particles per unit area relative to the sample surface.

The rechargeable battery pack 74 allows the unit to run for about 2 hours of continuous use or 8 hours in normal intermittent use. The system can also run on AC power for stationary applications. The system is targeted to weigh less than 16 lbs. The battery powered, lightweight unit and convenient carrying handle results in a truly portable unit that will enable the user to access areas that previously were difficult to access and to reduce the setup time.

Figure 4:
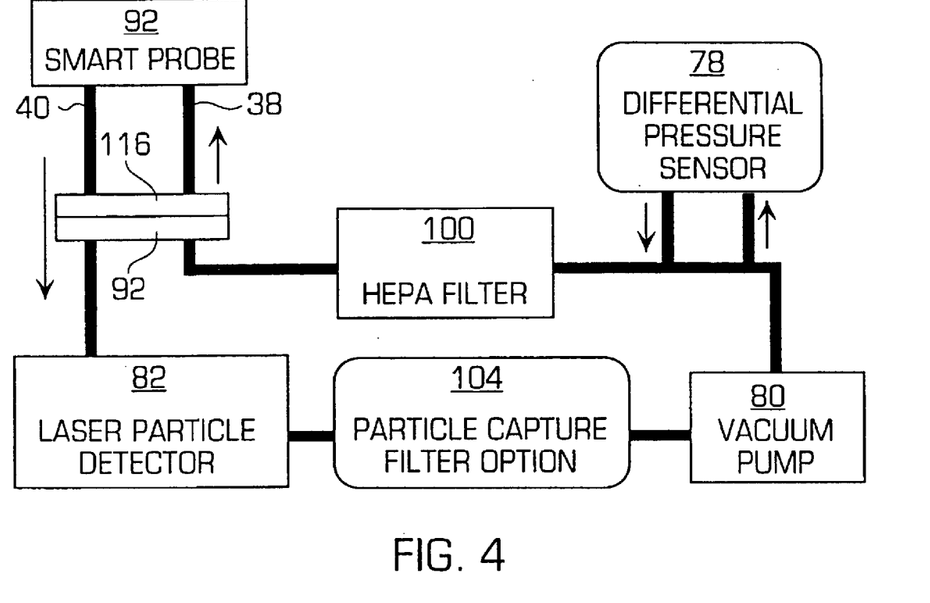
FIG. 4 is a schematic diagram showing the airstream path in the particle detector of the present invention.

FIG. 4 illustrates the airstream path of the particle detector device 10. The airstream plumbing is a substantially closed loop system, where clean air is supplied to the scanner probe 16 and particles are returned in the air stream that feeds the particle detector 82. An intake of the vacuum pump 80 is plumbed to the discharge side of the particle detector 82, with an optional particle capture filter 104 plumbed between the vacuum pump 80 and the particle detector 82. Plumbed to the discharge side of the vacuum pump 62 is a (HEPA) filter 100 that filters out particles from the flowing air, and an airflow measurement device (such as a differential pressure sensor) 78 that measures the rate of airflow through the system (using a controlled orifice in the airstream path). The discharge side of the filter 100 is plumbed to the supply tube 38 to supply filtered air to the exhaust holes 64 of the scanner probe 16.

The vacuum pump 80 creates a partial vacuum through the particle detector 82, return tube 40 of conduit 18, and to the scanner opening 62. The partial vacuum draws air from the sample surface to the particle detector 82, which is preferably a laser diode light scattering counter known in the art that determines particle count and size. After the particles are analyzed, they are filtered from airstream either by capture filter 104 or HEPA filter 100, whereafter the airstream is returned to the sample surface via smart probe 92.

Differential pressure sensor 78 measures the rate of airflow through the system. Controller 90 adjusts the speed of vacuum pump 80 to maintain the flow rate at the desired level. Flow rate control is important for several reasons. First, for accurate measurements, the flow rate should be the same for each particle measurement for a given scanner probe. Second, different probes 92 will require different flow rates for maximum accuracy. Third, when the probe 92 is scanned across the surface, additional pressure (back pressure) is imposed on the system, both initially as the probe is placed on the surface and as the texture or shape of the surface changes during the scan. It is therefore important to maintain the proper and constant flow rate throughout the entire scan to effectively remove particles from the surface and maintain a high sensitivity for the system.

Figure 5:
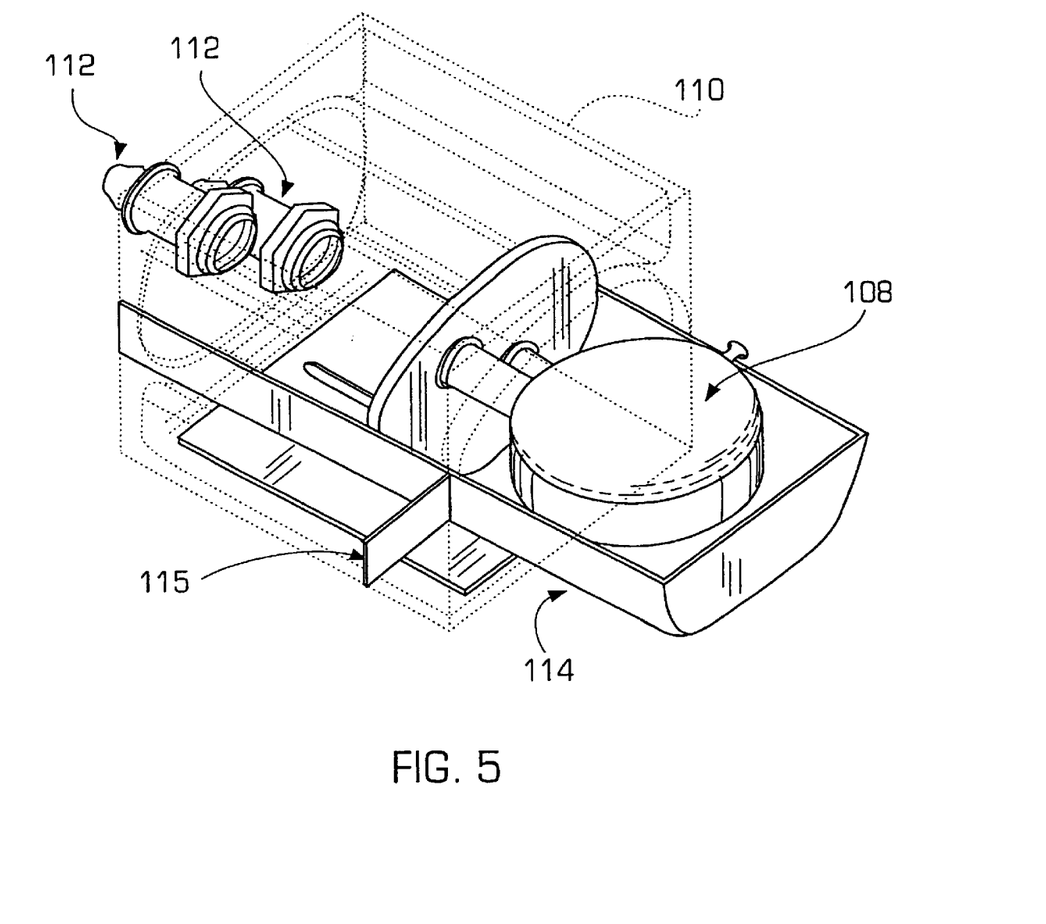
FIG. 5 is a partially broken away view of the particle capture filter cartridge and tray of the present invention.

The particle capture filter 104 is a removable filter element inserted into the airstream path to capture the particles in the airstream that have just passed through and been counted by the laser particle detector 82. This allows the user to not only measure the surface cleanliness, but to capture the counted particles for laboratory analysis and identification. In the preferred embodiment, the capture filter 104 is a membrane filter element that is disposed in a sealable, disposable cartridge 108 that inserts into a receptacle 110 connected to the system airstream, as illustrated in FIG. 5. The receptacle 110 and cartridge 108 have pneumatic quick disconnect connectors 112 that mate to connect the filter element 104 to the system airstream. Connectors 112 on the cartridge 108 can be manually capped after being disengaged from the system to prevent contamination of the filter element 104 until laboratory analysis can be performed. The filter cartridge 108 is installed and removed by means of a pullout tray 114 that is similar to a CD ROM. The tray 114 pops partially out from the receptacle 110 when a release button 115 is depressed. The tray 114 is then manually fully opened, and the removable filter cartridge 108 can be installed or removed. A dummy cartridge identical to cartridge 108 but with no filter element 104 inside can be inserted into the receptacle 110 if no capture filter 104 is needed. Sensors, preferably optical sensors, automatically identify the presence or absence of the cartridges, and whether the cartridge includes a filter 104 or is a dummy cartridge. This data is recorded along with the sample record. The vacuum pump 80 is deactivated if no cartridge is detected. The cartridge 108 is sealed when removed from the system, so that it can be sent to an analytical laboratory for analysis of the contamination trapped by the filter media 104.

Figure 6:
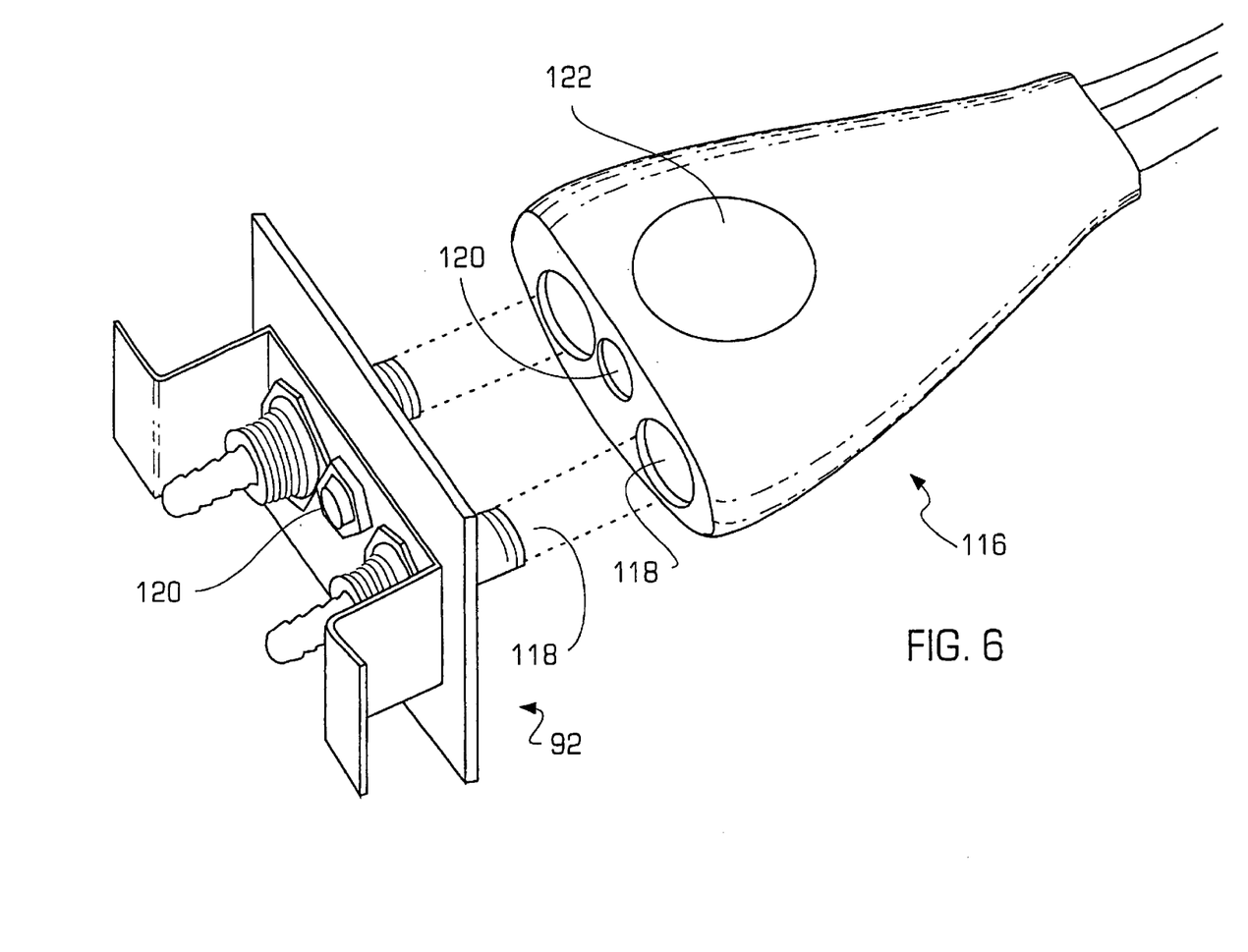
FIG. 6 is a partially exploded view of the quick release connection between the conduit and the particle counter assembly of the present invention.

The connection between the conduit 18 and the particle counter assembly is illustrated in FIG. 6. Single quick-release connector 116 and smart probe port 92 are used for both electrical and pneumatic connections. The conduit 18 terminates in the quick release multiconnector 116 that releasably engages with smart probe port 92, each of which has pneumatic quick disconnect connectors 118 for connecting the air supply and return tubes 38/40 to the plumbing of the particle counter assembly 12. Preferably, these quick disconnect connectors 118 are self sealing when disengaged to prevent contamination of the system airstream tubing. Connector 116 and port 92 also include electrical connectors 120 for supplying power to, and gathering data and signals from, the probe 16 via conduit electrical wiring 44 (i.e. to operate LED 54 and run switch 36). Connector 116 includes a release button 122 for quickly releasing the connector from the port 92.

Different sizes and types of probes 16 can be used to test different sized or shaped surface areas. Each probe type/size may require a different flow rate and/or a different set of calculations for data analysis. For example, ½ inch, 2-inch and 3-inch diameter scanner probes 16 have been used, some of which need different flow rates to operate correctly. The ½ inch probe may need about ½ cubic feet per minute (CFM) flow rate, while the 2 and 3 inch probes may need 1 CFM. Probes 92 may be called 'smart' probes because they include electronic indicia that allows the system controller 90 to automatically recognize one or more characteristics of the probe, such as its size and/or type. The electronic indicia could be an IC chip, electrical circuitry or simply predetermined combinations of electrical pin connections in the probe 16, in the conduit 18, or in the multiconnector 116 that is unique to the size/type of probe identified thereby. The controller automatically displays the probe type/size on the control screen, operates the vacuum pump 80 to generate the proper flow rate, and applies the proper formulas for calculating the particle detection results given the electronic indicia identified by the system controller 90.

Figure 7A:
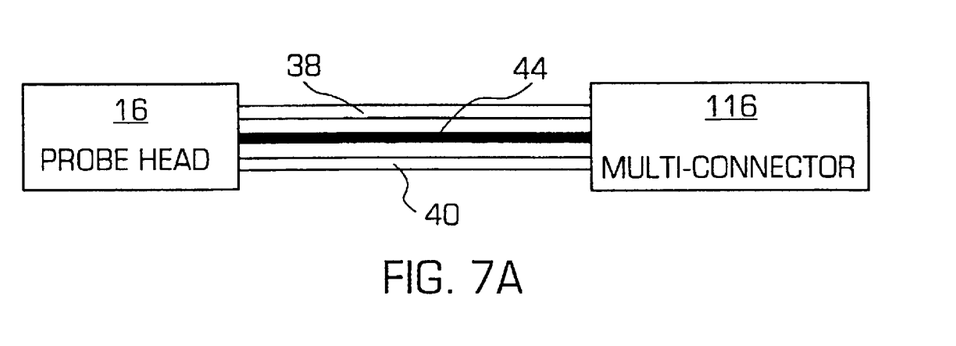
FIGS. 7A and 7B are schematic diagrams showing the pneumatic tubing and electrical wiring of the conduit for the scanner head and purge filter head, respectively, of the present invention.
Figure 7B:
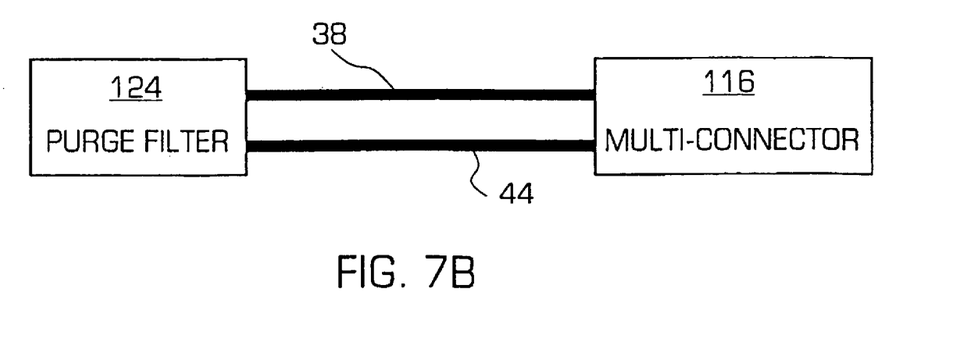

FIG. 7A illustrates the tubing 38/40 and electrical wiring 44 running between the multiconnector 116 and probe head 16. FIG. 7B illustrates a purge filter 124 that can be attached to the system to clean out accumulated particles from the air lines in the system. The purge filter plugs into the system in the same way probe 16 does, although there is no need for electrical wiring 44 all the way to the purge filter itself. Purge filter 124 completely closes the airstream loop of the system, which can be run to filter out any particles in the system using purge filter 124, the HEPA filter 100 and the particle capture filter 104 (if connected). Preferably, purge filter 124 filters particles out that are as small as 0.3 microns. The controller 90 will automatically recognize the absence of or type of probe attached to the system, including the purge filter, and run the system accordingly. For example, the vacuum pump 80 is deactivated if no probe or purge filter is detected.

Figure 8A:
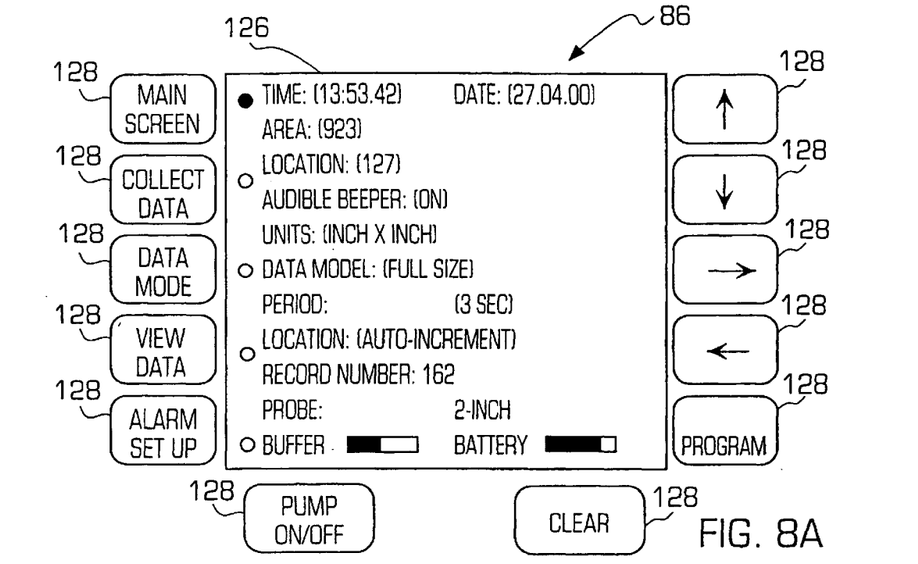
FIGS. 8A to 8F are front views of the control panel and display of the present invention, illustrating the various screens produced by the display.
Figure 8B:
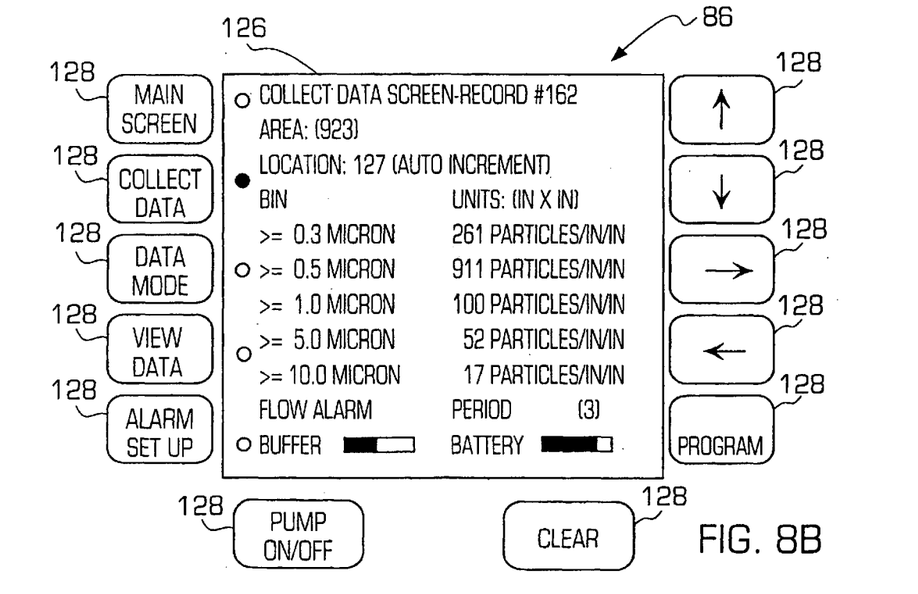
Figure 8C:
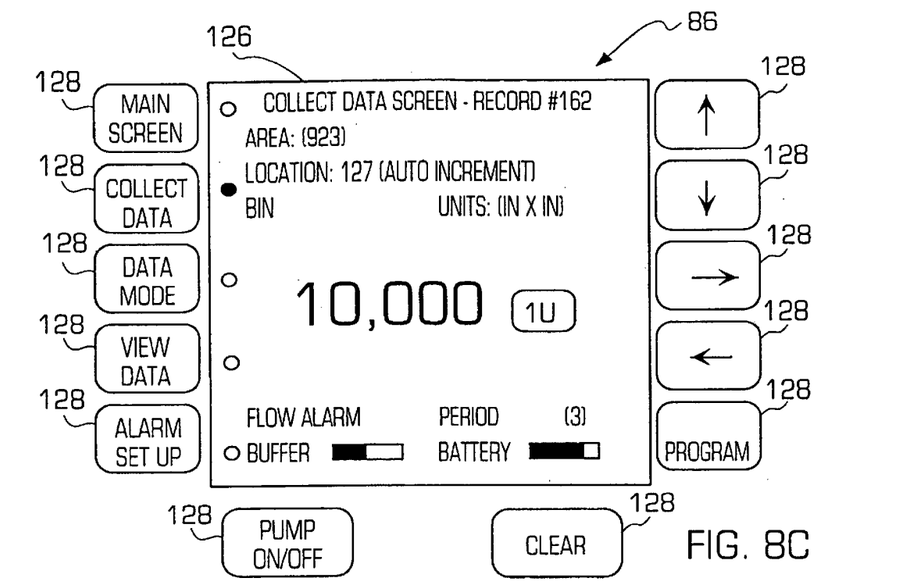
Figure 8D:
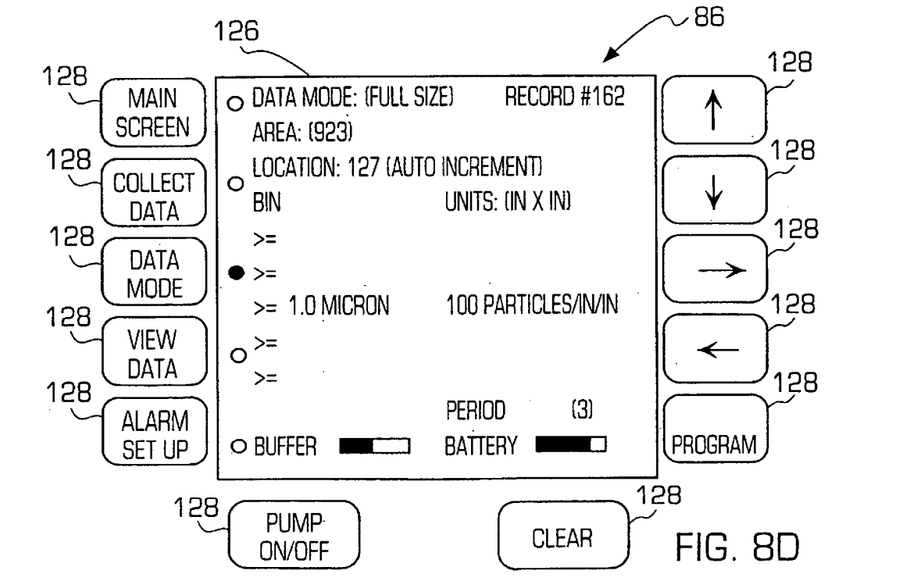
Figure 8E:
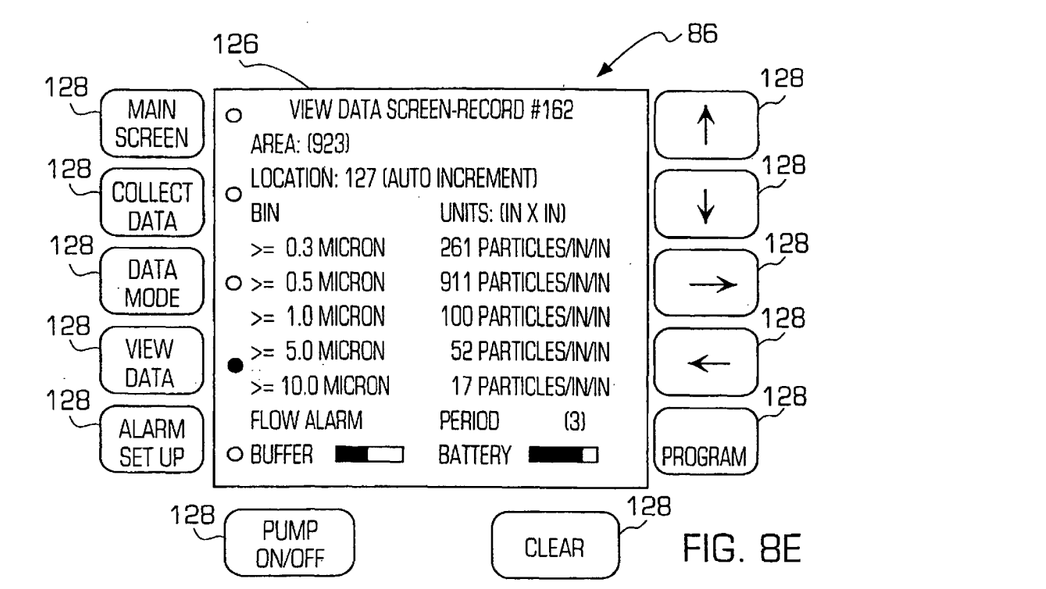
Figure 8F:
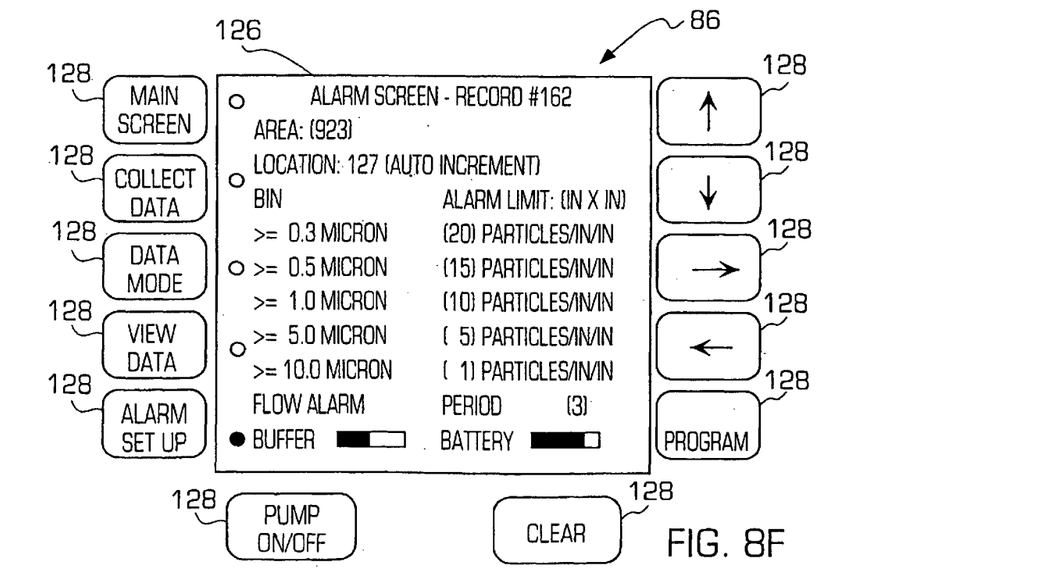

The particle counter assembly 12 includes a front display panel 86 that is exposed by the aperture 26 in front cover 24. This front display panel is shown in FIGS. 8A to 8F, and includes a multicolor screen 126 and a series of touch screen buttons 128 for operating the system. The preferred embodiment includes five screen navigation buttons to select from five different screens (Main: shows overview of system (FIG. 8A); Collect Data: shows current or last particle count data (FIG. 8B); Data Mode: allows user to choose normal full screen (FIG. 8D) or enlarged data modes (FIG. 8C) to better view critical data; View Data: shows previously recorded data (FIG. 8E); and Alarm Setup: allows user to set up alarm limits for each particle size (FIG. 8F).) There is also a Pump On/Off button (for activating/deactivating the vacuum pump 80), a Clear button (for clearing the highlighted field), and Navigation buttons (arrow buttons for moving a cursor and a Program button for saving selections on the screen). The large color screen enables the operator to comfortably view a large amount of data, or switch to the "zoom" screen to see only critical count data from a distance. Buttons 128 can be either hard wired keys, or soft keys displayed on a touch-sensitive type display screen 126.

The calibration port 94 allows a calibration technician to perform a normal calibration to the laser particle detector 82 without having to open the unit. Data collected is then stored in the particle detector 10. The system has RS-232 serial and Ethernet communication capability via the data port 98, so that collected data can be imported into a customers' network or host computer. Data port 98 can also allow the unit to communicate through a network or directly with the internet, which would allow remote access to the unit and the data stored therein, as well as data or instructions that can be displayed on a computer screen. The preferred embodiment also includes multiple levels of password protected access (e.g. factory, owner, user, etc.), with each password level having different rights to make changes to the system or to access certain data.

The scanner base 30 is preferably perpendicularly connected (but could instead be attached in a parallel fashion) to the scanner handle 34 which includes a control section 52 having the run switch 36 and an LED light 54 for indicating whether the device is counting particles. Activating the pump on/off button on the control panel activates the vacuum pump 80, which should be run for a minute or two before data is collected. In a preferred embodiment of the invention, activating the run switch 36 while the system is in its standby mode (vacuum motor running but particle counting not activated) causes the system to go into its "counting" mode where particle measurements take place for a predetermined time period (e.g. 3 seconds) and the LED light 54 is activated. After the expiration of the predetermined time period, particle measurements cease and the LED light 54 is deactivated. Audible signals can also be produced to indicate when the instrument is switching between its "counting" and its "standby" modes.

The device described above is used to obtain a relative cleanliness level by quantitating the released particles from surfaces. Examples of possible test surfaces include tables, shelves, walls, ceilings, benches, product containers or virtually any other kind of surface. Different scanner geometries can be employed for customizing the device to the particular sample surface of interest. The technique can be used to verify cleanliness prior to undertaking some type of clean room procedure. The technique can also be used to evaluate or compare the effectiveness of various cleaning techniques and products.

In a preferred embodiment of the invention, filtered air is used to disturb the surface particles and a vacuum system collects the particles which are fluidized by the air. Particle levels are measured and recorded in particles per centimeters squared or particles per inch squared using optical/laser technology. The device of the present invention is capable of detecting particles as small as 0.3 microns. The air is filtered to 0.2 microns and supplied to the scanner head, where the same amount of air is pulled through the scanner head to the sensing system for counting and sizing.

Prior to counting particles, the system should first be checked for zero counting by holding the scanner head towards the clean room supply air and taking repeated counts until the levels are below 5 particles per inch squared. The scanner head is then passed over the sample surface at a rate of 10 LFPM (2 LIPM) for a period of three or six seconds. The test cycle is started from the run switch 36 located in the scanner probe 16. The scanner probe 16 is moved lightly across the surface assisted by the fluidizing air.

As this method gives relative cleanliness levels immediately, it is recommended that routine monitoring be performed with historical data being logged for various surfaces and locations in the clean room. It is also recommended that a minimum of six readings be taken for any given area with average levels and maximum allowable single reading levels being established for the various surfaces and areas.

It is to be understood that the present invention is not limited to the embodiment(s) described above and illustrated herein, but encompasses any and all variations falling within the scope of the appended claims.

What is claimed is:

1. A device for counting particles on a sample surface, comprising:
    a scanner having at least one opening for receiving particles from a sample surface;
    a particle counter for counting particles passed therethrough;
    a conduit having a first end connected to the scanner and a second end connected to the particle counter, wherein the conduit includes first and second tubes;
    the particle counter includes:
        a pump for producing an airstream flowing from the scanner opening, through the first tube, through the particle counter, and back to the scanner via the second tube, for carrying the particles to the particle counter for quantitation;
        a heat-sink for dissipating heat generated by the pump; and
        a circulating fan for normalizing air temperature inside the particle counter;
    a sensor for measuring a rate of flow of the airstream; and
    a controller for controlling a speed of the pump in response to the measured rate of flow of the airstream to maintain the airstream at a constant flow rate while the particle counter quantitates the particles in the airstream.

2. The device of claim 1, further comprising:
    a filter for filtering the airstream before the airstream flows back to the scanner.

3. The device of claim 2, wherein the particle counter further comprising:
    a particle detector for counting the particles in the airstream coming from the scanner;
    a filter cartridge port through which the airstream flows after passing through the particle detector; and
    a filter cartridge removably connected to the filter cartridge port for capturing the particles from the airstream after being counted by the particle detector.

4. The device of claim 1, wherein the particle counter further comprises a rechargeable battery for powering the pump, the sensor and the controller.

5. A device for counting particles on a sample surface, comprising:
- a scanner having at least one opening for receiving particles from a sample surface;
- a particle counter for counting particles passed therethrough;
- a conduit having a first end connected to the scanner and a second end connected to the particle counter, wherein the conduit includes first and second tubes;
- the particle counter includes a pump for producing an airstream flowing from the scanner opening, through the first tube, through the particle counter, and back to the scanner via the second tube, for carrying the particles to the particle counter for quantitation;
- a sensor for measuring a rate of flow of the airstream; and
- a controller for controlling a speed of the pump in response to the measured rate of flow of the airstream to maintain the airstream at a constant flow rate while the particle counter quantitates the particles in the airstream, wherein the controller provides different levels of password protected access for different sets of data.

6. The device of claim 5, wherein the particle counter further comprises a touch sensitive display screen for displaying data and softkeys for operating the particle counter.

7. The device of claim 6, wherein the display screen includes a zoom mode in which selected displayed data is magnified.

8. The device of claim 5, wherein the particle counter further comprises a data port for remote access to data stored by the particle counter via at least one of an external computer and an external network.

9. A device for counting particles on a sample surface, comprising:
- a scanner having at least one opening for receiving particles from a sample surface;
- a conduit having a first end connected to the scanner and a second end terminating in a first connector, wherein the conduit includes first and second tubes;
- a particle counter for counting particles passed therethrough, the particle counter including:
  - a port for receiving the first connector, and
  - a pump for producing an airstream flowing from the scanner opening, through the first tube, through the particle counter, and back to the scanner via the second tube, for carrying the particles to the particle counter for quantitation;
- electronic indicia disposed in at least one of the first connector, the conduit and the scanner for identifying at least one characteristic of the scanner; and
- a controller for detecting the electronic indicia via the port and first connector, and for controlling the particle counter in response to the detected electronic indicia.

10. The device of claim 9, wherein the at least one characteristic includes a size of the scanner.

11. The device of claim 9, wherein the controller adjusts the speed of the pump in response to the detected electronic indicia.

12. The device of claim 9, wherein formulas used by the controller to calculate data analysis from the counted particles is varied in response to the detected electronic indicia.

13. The device of claim 9, wherein the first connector and port seal themselves when disconnected from each other.

14. The device of claim 9, further comprising a release button that unlatches the first connector from the port.

15. The device of claim 9, further comprising:
- a purge filter for filtering airflow passed therethrough;
- a second conduit having a first end connected to the purge filter and a second end terminating in a second connector, wherein the conduit includes first and second tubes, and wherein the second connector is connectable to the port so that when the pump is activated, the purge filter filters contamination from the particle counter.

16. A device for counting particles on a sample surface, comprising:
- a scanner having at least one opening for receiving particles from a sample surface;
- a particle counter for analyzing particles passed therethrough;
- a conduit having a first end connected to the scanner and a second end connected to the particle counter, wherein the conduit includes first and second tubes;
- the particle counter includes:
  - a pump for producing an airstream flowing from the scanner opening, through the first tube, through the particle counter, and back to the scanner via the second tube, for carrying the particles to the particle counter,
  - a particle detector for counting the particles in the airstream coming from the scanner,
  - a filter cartridge port through which the airstream flows after passing through the particle detector,
  - a filter cartridge removably connected to the filter cartridge port for capturing the particles in the airstream after being counted by the particle detector, and
  - a filter for filtering the airstream before the airstream flows back to the scanner.

17. A device for counting particles on a sample surface, comprising:
- a scanner having at least one opening for receiving particles from a sample surface;
- a particle counter for analyzing particles passed therethrough;
- a conduit having a first end connected to the scanner and a second end connected to the particle counter, wherein the conduit includes first and second tubes;
- the particle counter includes:
  - a pump for producing an airstream flowing from the scanner opening, through the first tube, through the particle counter, and back to the scanner via the second tube, for carrying the particles to the particle counter,
  - a particle detector for counting the particles in the airstream coming from the scanner,
  - a filter cartridge port through which the airstream flows after passing through the particle detector,
  - a filter cartridge removably connected to the filter cartridge port for capturing the particles in the airstream after being counted by the particle detector,
  - a sensor for detecting the presence of the filter cartridge in the filter cartridge port; and
  - a controller for controlling the pump in response to the sensor.

18. The device of claim 17, wherein the particle counter further comprising:
- a dummy cartridge removably connectable to the filter cartridge port for passing the airstream without filtration, wherein the sensor detects the presence of the dummy cartridge in the filter cartridge port.

* * * * *